United States Patent [19]

Schwarz et al.

[11] Patent Number: 4,910,012
[45] Date of Patent: Mar. 20, 1990

[54] PRODUCTS CONTAINING TC-99-M-ωALKYLPHOSPHINICO-1-HYDROXYALKANE-1,1-DIPHOSPHONATES FOR BONE SCINTIGRAPHY AND A PROCESS FOR THE PREPARATION OF THESE PRODUCTS

[75] Inventors: Alexander Schwarz, Flösheim am Main; Axel Steinsträsser, Liederbach, both of Fed. Rep. of Germany

[73] Assignee: Hoechst Aktiengesellschaft, Frankfurt am Main, Fed. Rep. of Germany

[21] Appl. No.: 329,477

[22] Filed: Mar. 28, 1989

[30] Foreign Application Priority Data

Mar. 30, 1988 [DE] Fed. Rep. of Germany ....... 3810819

[51] Int. Cl.[4] ...................... A61K 49/02; C07F 13/00
[52] U.S. Cl. ......................................... 424/1.1; 534/14
[58] Field of Search ............................ 424/1.1; 534/14

[56] References Cited

U.S. PATENT DOCUMENTS 3,851,044  11/1974  Adler et al. ............................ 424/1.1
4,515,766   5/1985  Castronovo et al. ................ 424/1.1
4,693,884   9/1987  Kleiner et al. ........................ 424/1.1

*Primary Examiner*—John S. Maples
*Attorney, Agent, or Firm*—Finnegan, Henderson, Farabow, Garrett and Dunner

[57] ABSTRACT

Tc-99m products containing at least one compound of the formula I

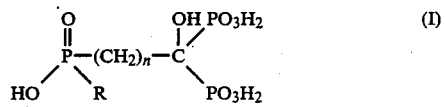

in which R is a methyl, ethyl or propyl group and n represents a number from 1 to 6, or the physiologically tolerated salts thereof, are suitable for use in bone scintigraphy, especially for locating bone tumors.

8 Claims, 2 Drawing Sheets

PRODUCTS CONTAINING TC-99-M-ωALKYLPHOSPHINICO-1-HYDROXY-ALKANE-1,1-DIPHOSPHONATES FOR BONE SCINTIGRAPHY AND A PROCESS FOR THE PREPARATION OF THESE PRODUCTS

The present invention relates to products containing Tc-99m-ω-alkylphosphinico-1-hydroxyalkane-1,1-diphosphonates for bone scintigraphy and to a process for the preparation of these products.

Among methods in nuclear medicine, skeletal scintigraphy has acquired particular importance because it is now possible with its aid to diagnose bone diseases at an early stage, often before they are radiologically evident. The first Tc-99m-labelled osteotropic compounds were inorganic polyphosphates, but these have a relatively slow clearance from the blood as a result of their tendency to hydrolyze to monophosphate in aqueous solution.

The introduction of the first organic diphosphonic acid by Yano et al. ("Tc-99m-labelled stannous ethane-1-hydroxy-1,1-diphosphonate -Tc-99m-HEDP- : a new bone scanning agent", J. Nucl. Med. 14, 73, 1973 and U.S. Pat. No. 3,735,001) was a considerable advance because, owing to the significantly quicker clearance of the Tc-99m-HEDP from the plasma, it was possible considerably to shorten the time between administration and the start of scintigraphy. The two phosphoric acid groups in this substance are linked together via a carbon atom,

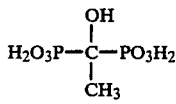

whereas an oxygen atom is present in its place in the polyphosphates. In subsequent years a large number of geminal diphosphonic acids which, labelled with technetium-99m, are suitable for skeletal scintigraphy has been described.

To date only three substances, methanediphosphonic acid (MDP), 3,3-diphosphono-1,2-propanedicarboxylic acid (DPD) and hydroxymethanediphosphonic acid (HMP), have found wide use in routine diagnosis in nuclear medicine.

However, maximum accumulation of the Tc-99m diphosphonate in healthy bone is not necessarily an advantage for improving the detection of skeletal lesions, especially of metastases in the early stage. Substances which are taken up only slightly in normal bone but sufficiently well in the lesion, and, moreover, are rapidly eliminated from the blood may be advantageous for detailed detection of lesions.

Many investigations carried out to date have been devoted to the search for compounds having a more favorable uptake ratio between the lesion and normal skeleton. Our investigations have revealed that out of a large number of tested products such as, for example, 1-amino-1,1-ethanediphosphonic acid (A-EDP), N,N-dimethylaminomethanediphosphonic acid (DMA-MDP), N-ethylaminomethanediphosphonic acid (EA-MDP), N,N-diethylaminomethanediphosphonic acid (DEA-MDP) and N,N-dibutylaminomethanediphosphonic acid (DBA-MDP) the last-mentioned compound has by far the highest ratios Q for the uptake of Tc-99m in a lesion by comparison with the uptake in normal bone (Q=(% Tc/g of lesion)/(% Tc/g of normal bone)). This result has also been confirmed by Schümichen (C. Schümichen et al. Nucl. Med. 27, 8–11, 1988) who found, when comparing the Tc accumulation of DBA-MDP, DPD, and MDP which is most commonly used commercially, in bone lesions and normal bone, that the accumulation of DBA-MDP in the lesions was distinctly higher.

However, the product DBA-MDP which, according to the current state of knowledge, is the best for the said purposes, has the disadvantages that the blood clearance is not optimal and thus the bone/background ratio is relatively poor. Hence there is a need to make better products available for bone scintigraphy, especially for detecting skeletal lesions.

It has now been found, surprisingly, that Tc-99m-ω-alkylphosphinico-1-hydroxyalkane-1,1-diphosphonates are outstandingly suitable for the said purposes.

Accordingly, the invention relates to Tc-99m products for bone scintigraphy, which contain at least one compound of the formula I

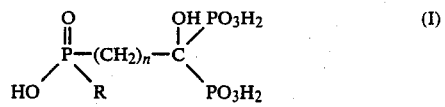

in which R is a methyl, ethyl or propyl group, and n is a number from 1 to 6, and which may be in the form of a physiologically tolerated salt. As a rule, the Tc-99m products according to the invention contain only one compound of the formula I or one of the salts thereof.

Preferred compounds of the formula I are those in which R is a methyl or ethyl group, and n is a number from 1 to 3. A particularly preferred compound is the one in which R is a methyl group and n equals 2, i.e. the compound of the formula

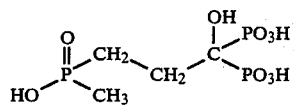

which is called 1-hydroxy-3-methylphosphinico-1,1-propanediphosphonic acid (HMPD), or the physiologically tolerated salts thereof. Suitable physiologically tolerated salts are the alkali metal salts, especially the Compared with the compound DBA-MDP, which may be regarded as the best compound of the state of the art for detecting skeletal lesions, the said compounds have the advantage that they have a distinctly higher lesion quotient Q (cf. Example 5) and that they are distinguished by being more quickly cleared from the blood, as our own experiments have shown.

The compounds which can be used according to the invention are preferably prepared by the process described in German Patent Application P No. 38 05 644.5.

Additionally preferred are Tc-99m products, as described above, which contain a tin(II) compound. Particularly suitable tin(II) compounds are SnO and SnCl$_2$, which are added in a molar ratio of about 1:100 to about 1:2, preferably of about 1:20, to the compound of the formula I.

The addition of tin(II) ions is necessary in order to achieve rapid and, where possible, quantitative reduction and binding of the radionuclide, which is added as $^{99m}TcO_4^-$, to the active substance (diphosphonate).

It may furthermore be expedient to add a stabilizer to the Tc-99m product. A particularly suitable stabilizer is N-(4-aminobenzoyl)glutamic acid or the sodium salt thereof, especially in a molar ratio of 0.5:10 to 2:10 to the compound of the formula I or the salt thereof.

A particularly suitable product is one which contains tin(II),N-(4-aminobenzoyl)-L-glutamic acid (ABG) and 1-hydroxy-3-methylphosphinico-1,1-propanediphosphonic acid (HMPD) in the molar ratio of about 1:2:20 and which, after labeling with technetium-99m, has as injectable solution a pH of about 6–7.

The invention additionally relates to a process for the preparation of a Tc-99m product, which comprises adding a tin(II) compound to a solution of a compound of the formula I, or one of the salts thereof, and adding a pertechnetate solution to the mixture. It is expedient for the tin(II) compound to be dissolved before the addition, for example $SnCl_2.2H_2O$ in dilute mineral acid, for example hydrochloric acid, or tin(II) oxide in alkali metal hydroxide, preferably in sodium hydroxide solution. The compound of the formula I, or the salt thereof, is likewise preferably used in aqueous solution. In addition, the stabilizer is expediently added. The individual reagents are added in any desired sequence, and this ought to take place with exclusion of air. The individual reagents should preferably be added in a ratio of amounts such that a pH of about 6–8, preferably of about 7, results. The content of the compound of the formula I, or the salts thereof, in solution can vary within wide limits; the preferred content is about 10–30 mg/ml of solution.

The Tc-99m-pertechnetate solution, which can be obtained from a Tc-99m generator, is added to the solution prepared as described. A preferred Tc-99m generator is described in German Patent Application P 35 31 355.2. It is particularly expedient before the addition of the Tc-99m solution to freeze-dry the solution which has been prepared as described, preferably in individual glass vessels whose contents correspond to one labeling unit. The last-mentioned procedure has the advantage that it is possible to add freshly eluted Tc-99m-pertechnetate solution immediately before use to a labeling unit which is stable and can be stored for months.

The invention additionally relates to an method for the scintigraphic visualization of the skeleton, especially for locating bone tumors, which comprises a Tc-99m product according to the invention being administered to the body intravenously and then the radioactivity distribution in the body being measured. The amount of Tc-99m compound to be injected can vary over a wide range; it should preferably be in the range 0.005 mg–0.1 mg per kg of body weight, particularly preferably between 0.01 mg and 0.03 mg per kg of body weight. For an adult patient the injected amount ought preferably to contain a radioactivity dose of about 100–900 MBq, particularly preferably of about 500 MBq (about 15 mCi).

The radioactivity distribution can be determined using generally known apparatus (gamma cameras, cf. C. Schümichen: Physiologische Grundlagen der Knochenszintigraphie; Messtechnik und quantitative Auswertung, Der Nuklearmediziner 7, 73–88, 1984).

EXAMPLE 1

40 mg of $SnCl_2\times 2H_2O$, dissolved in 1 ml of 0.1 N hydrochloric acid, and 100 mg of monosodium N-(4-aminobenzoyl)-L-glutamate, dissolved in 5 ml of water, were added to an aqueous solution of 1.134 g of 1-hydroxy-3-methylphosphinico-1,1-propanediphosphonic acid monosodium salt monohydrate with exclusion of air. The clear solution was adjusted to pH 6 by addition of sodium hydroxide solution and was diluted with water to a total volume of 50 ml, filtered sterile and dispensed in 0.5 ml portions, corresponding to 10 mg of HMPD. The freeze-dried samples were labeled by addition of eluate from a Tc-99m generator (pertechnetate solution), and 0.01 mg portions in 0.1 ml (about 1 MBq) were injected i.v. into rats. The results of the organ distribution are compared with those of Example 2 in Table 2.

EXAMPLE 2

18.5 ml of 2N sodium hydroxide solution were placed in a 100 ml flask, and 110 mg of tin(II) oxide were added and dissolved therein completely at room temperature. While excluding air, a solution of 5.67 g of 1-hydroxy-3-methylphosphinico-1,1-propanediphosphonic acid monosodium salt monohydrate and 0.45 g of N-(4-aminobenzoyl)-L-glutamic acid (ABG) in 60 ml of water were added to this sodium stannite solution. After this solution, which had a pH of 7, had been thoroughly mixed it was adjusted to a total volume of 250 ml with water. The solution was filtered sterile and introduced into individual vials and freeze-dried. Each container (labeling unit) contained:
10 mg of HMPD,
0.2 mg of $Sn^{2+}$ and
0.9 mg of ABG.

EXAMPLE 3

The labeling yield of Tc-99m-HMPD was determined, and the purity and stability were tested, by thin-layer chromatographic methods, gel filtration and HPLC.

1. The labeling yield was determined by measuring the proportion of free pertechnetate (a) and the content of reduced unbound technetium (b) by thin-layer chromatography.
  (a) The $^{99m}TcO_4^-$ was determined on silica gel fiber glass plates (ITLC type SG, manufactured by Gelman, Michigan, USA) using methyl ethyl ketone as eluent (pertechnetate $R_f=1$) and
  (b) the reduced unbound technetium ($^{99m}Tc^{4+}$) was determined on an identical plate using 2 M sodium acetate solution as eluent ($Tc^{4+}R_f=0$). The proportion of both impurities in the injectable solution was always $<1\%$.

Figure 1:
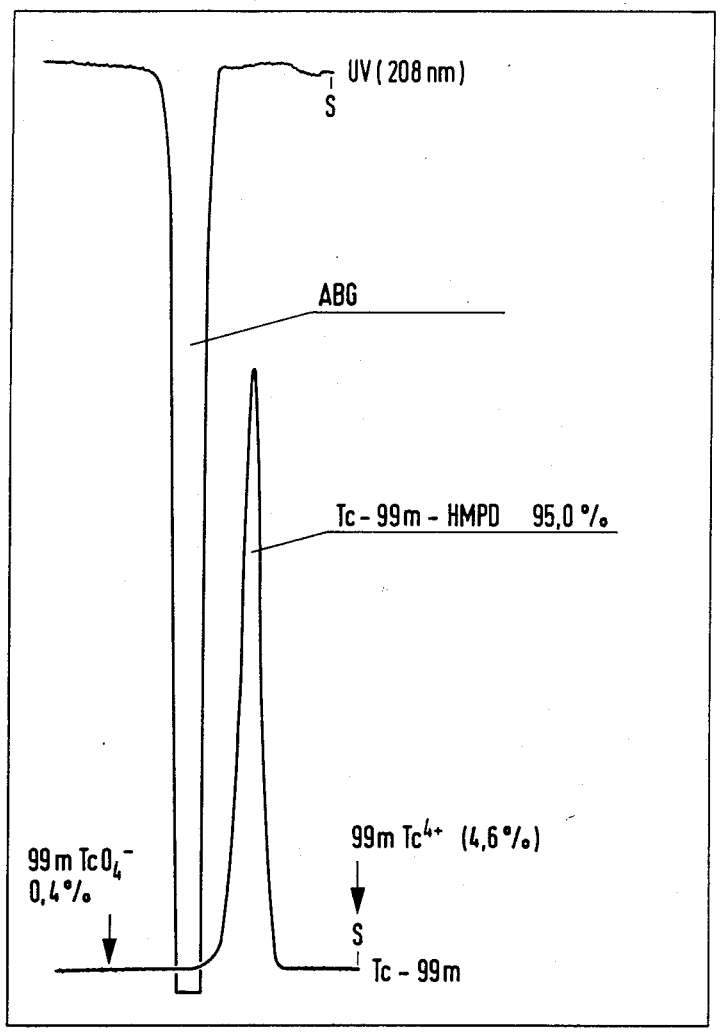
FIG. 1 is a stability test of Tc-99m-HMPD and
FIG. 2 is a purity test of Tc-99m-HMPD by HPLC The invention is to be explained in detail by the exemplary embodiments which follow.

2. The stability for a period of up to 24 h after preparation was tested by gel chromatography on polyacrylamide gel (Bio Gel ® P-10, manufactured by Bio-Rad, California, USA) using 0.9% NaCl solution as eluent (FIG. 1). The proportion of the activity in the HMPD, that in the form of pertechnetate and that remaining on the column were measured (Table 1). The latter is greater than the proportion of $^{99m}$-$Tc^{4+}$ because nonspecific adsorption of technetium to the support material is always observed.

TABLE 1

| Time after preparation | % Activity in the HMPD | % Tc-99m as pertechnetate | Residue on the column |
|---|---|---|---|
| 5 min | 92.6 | 0.6 | 6.8 |
| 2 h | 92.1 | 0.4 | 7.5 |
| 7 h | 95.0 | 0.4 | 4.6 |
| 24 h | 94.0 | 0.8 | 5.2 |

Figure 2:
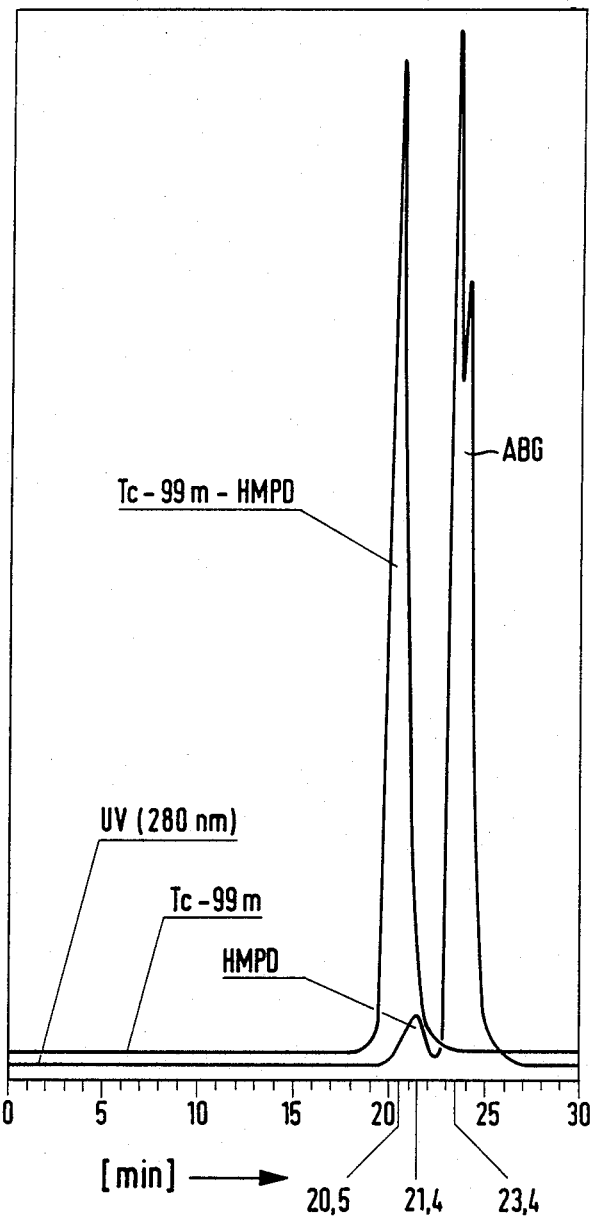

3. The HPLC testing (FIG. 2) shows a radiochemically pure Tc-99m-HMPD (retention time 20.5 min). HMPD (UV trace) differs from the labeled form by a somewhat longer retention time (21.4 min) whereas the unlabeled stabilizer ABG is separated at 23.4 min.

The data show that the proportion of Tc-99m activity present in the HMPD is more than 90% and that the product is stable for a whole working day.

EXAMPLE 4

In order to examine the utility of the different HMPD preparations in terms of their suitability for skeletal scintigraphy, their organ distribution in rats 2 hours after injection was measured (Table 2):

TABLE 2

Organ distribution of Tc-99m-HMPD in the rat (n = 3) 2 h after i.v. injection as a % of the administered test dose per organ or tissue

| | Tc-99m-HMPD | |
|---|---|---|
| | Preparation of Example 1 pH 6 | Preparation of Example 2 pH 7 |
| Bone (5%)* | 21.3 | 31.0 |
| Liver | 0.16 | 0.17 |
| Lung | 0.054 | 0.069 |
| Spleen | 0.011 | 0.010 |
| Kidneys | 0.83 | 0.77 |
| Blood (7%)* | 0.5 | 0.4 |
| Muscle (40%)* | 0.4 | 0.6 |
| Urine | — | 59.5 |
| Intestine | 1.2 | 1.1 |
| Stomach | 0.18 | 0.14 |
| Thyroid | 0.008 | 0.007 |

*% of body weight

The comparison shows that a difference in the pH of the injectable product and in the mode of perparation (Example 1 or 2) results in a distinct difference in the uptake in normal bone. The product prepared as in Example 2 (pH=7) was used for the following experiment.

In contrast to other diphosphonates, as well as to pyrophosphate, no increase in liver uptake at the expense of skeletal accumulation has been observed with Tc-99-mHMPD when the substance was administered in larger amounts (Table 3).

TABLE 3

Organ distribution of Tc-99m-HMPD in the rat (n = 3) 2 h after injection as a function of the amount administered (mg) and as a % of the injected dose per organ or tissue. The various HMPD amounts were administered i.v. in 0.1 ml (about 0.7 MBq).

| | Amount of MPD administered (mg) | | | |
|---|---|---|---|---|
| | 1 | 0.1 | 0.01 | 0.001 |
| Bone | 28.7 | 32.6 | 34.7 | 32.9 |
| Blood | 0.8 | 0.4 | 0.4 | 0.7 |
| Muscle | 1.1 | 0.6 | 0.6 | 0.8 |
| Thyroid | 0.007 | 0.011 | 0.008 | 0.008 |
| Stomach | 0.090 | 0.092 | 0.091 | 0.151 |
| Liver | 0.22 | 0.17 | 0.18 | 0.27 |
| Lung | 0.079 | 0.480 | 0.048 | 0.080 |
| Kidneys | 1.03 | 0.94 | 1.05 | 1.51 |

TABLE 3-continued

Organ distribution of Tc-99m-HMPD in the rat (n = 3) 2 h after injection as a function of the amount administered (mg) and as a % of the injected dose per organ or tissue. The various HMPD amounts were administered i.v. in 0.1 ml (about 0.7 MBq).

| | Amount of MPD administered (mg) | | | |
|---|---|---|---|---|
| | 1 | 0.1 | 0.01 | 0.001 |
| Bladder + urine | 59.1 | 56.9 | 55.6 | 54.1 |

EXAMPLE 5

Tc-99m-HMPD was tested on the model of osteosarcoma in Sprague-Dawley rats. The 7–12-day old animals underwent paratibial implantation in the right rear limb of a tumor induced with $^{144}$Ce (Delbrück 1983). The investigation was carried out 4 weeks after tumor implantation on a total of 30 animals. 1. Investigation schedule:

Day 1 Tc-99m-MDP (reference substance)
Day 3 Tc-99m-HMPD

In each case injection of 0.01 mg of substance i.v. in 0.05 ml containing 9.25 MBq of Tc-99m
Scintigraphy 1, 90 and 180 minutes after injection
Storage of the scintigraphic data for the evaluation 2. Evaluation
Measurement of whole-body activity from the scintigraphic data
Ratio (Q) of the count density per unit area in the tumor to that in the contralateral tibia
Comparison of the quotient $Q_{HMPD}$ with that for the products $Q_{MDP}$ and $Q_{DBA-MDP}$.

The experimental results are shown in Table 4.

TABLE 4

| Tc-99m complex | Lesion quotient |
|---|---|
| HMPD | 1.27 |
| DBA-MDP | 1.16 |
| MDP | 1.0 |

The significantly better Q value for Tc-99m-HMPD by comparison with Tc-99m-MDP, which is widely used commercially, as well as with Tc-99m-DBA-MDP, which has hitherto been regarded as optimal on the basis of lesion experiments, demonstrates that the compounds according to the invention are more suitable than the compounds of the state of the art for locating bone tumors.

We claim:

1. A Tc-99m product for bone scintigraphy, which contains Tc-99m complexed with at least one compound of the formula I $$\begin{array}{c} O \\ \| \\ P-(CH_2)_n-C \\ / \quad \backslash \quad \quad \backslash \\ HO \quad R \quad \quad PO_3H_2 \end{array} \quad \begin{array}{c} OH\ PO_3H_2 \\ | / \\ \\ \end{array} \quad (I)$$

in which R is a methyl, ethyl or propyl group, and n is a number from 1 to 6, or a physiologically tolerated salt thereof.

2. A Tc-99m product as claimed in claim 1, wherein R is a methyl group and n equals 2.

3. A Tc-99m product as claimed in claim 1, which contains a tin(II) compound.

4. A Tc-99m product as claimed in claim 1, which contains a stabilizer.

5. A Tc-99m product as claimed in claim 1, which contains as a stabilizer the sodium salt of N-(4-aminobenzoyl)glutamic acid in a molar ratio of 0.5:10 to 2:10 to the compound of the formula I, or the salt thereof.

6. A method for the visualization of bone tumors in a subject, which comprises introducing an effective amount of Tc-99m product for bone scintigraphy as claimed in claim 1 into the body and then determining the radioactivity distribution in the body.

7. A Tc-99m product as claimed in claim 1, which contains a compound of the formula I, or a salt thereof, and a tin(II) compound in a molar ratio of about 100:1 to about 2:1.

8. A Tc-99m product as claimed in claim 4 which contains a tin(II) compound in a molar ratio of about 20:1.

* * * * *